United States Patent
Poppe et al.

(10) Patent No.: US 6,436,924 B2
(45) Date of Patent: Aug. 20, 2002

(54) ANTIHISTAMINE LEUKOTRIENE COMBINATIONS

(75) Inventors: Hildegard Poppe, Dresden; Jürgen Engel, Alzenau; István Szelényi, Schwaig, all of (DE)

(73) Assignee: ASTA Medica AG, Dresden (DE)

( * ) Notice: Subject to any disclaimer, the term of this patent is extended or adjusted under 35 U.S.C. 154(b) by 0 days.

(21) Appl. No.: 09/784,640

(22) Filed: Feb. 15, 2001

(30) Foreign Application Priority Data

Feb. 17, 2000 (DE) .......................... 100 07 203

(51) Int. Cl.$^7$ ............................... A61K 31/55
(52) U.S. Cl. ................................... 514/217.05
(58) Field of Search ..................... 514/217.05

(56) References Cited

U.S. PATENT DOCUMENTS

| 3,813,384 A | 5/1974 | Vogelsang et al. | 260/239 |
|---|---|---|---|
| 5,164,194 A | 11/1992 | Hettche | 424/489 |
| 5,375,693 A | * 12/1994 | Woosley et al. | 514/317 |
| 6,242,179 B1 | 6/2001 | Shah et al. | |

FOREIGN PATENT DOCUMENTS

| DE | 689 04 475 | 1/1993 |
|---|---|---|
| EP | 345 931 | 1/1993 |
| WO | WO 97/28797 | 8/1997 |
| WO | WO 98/34611 | 8/1998 |
| WO | WO 98/48839 | 11/1998 |
| WO | WO 99/32125 | 7/1999 |
| WO | WO 99/52554 | 10/1999 |

OTHER PUBLICATIONS

Yamasaki et al.; Involvement of Thromboxane $A_2$ and Histamine, etc., The Journal of Pharmacology, etc., vol. 280, 1997, 1471–79.

Braga da Motta et al.; Drug Modulation of Antigen–Induced Paw Oedema, etc., Br. J. Pharmacol. 1994. 111–116.

Yamasaki et al., Involvement of Thromboxane, etc., The Journal of Pharmacology, etc. vol. 280, No. 3 Braga da Motta et al., Br. J. Pharmacol (1994) 112, 111–11635, 99–107 (1999).

S. J. Tkachyk, MD, FRCPC, New treatments for allergic rhinitis, Canadian Family Physician, May 1999, vol. 45.

C. Bachert and B. Lange, Histamin und Leukotriene bei der allergischen Rhinitis, Pharmakologisches Forum, Allergologie, Jahrgang 22, Nr. 8/1999, S. 492–507.

* cited by examiner

*Primary Examiner*—James H. Reamer
(74) *Attorney, Agent, or Firm*—Goodwin Procter LLP

(57) ABSTRACT

The invention relates to a pharmaceutical composition for the treatment of allergic rhinitis, vasomotor rhinitis, and allergic conjunctivitis, which comprises (a) a nonsedating antihistamine or a pharmaceutically acceptable salt thereof, (b) a leukotriene $D_4$ antagonist, or a 5-lipoxygenase inhibitor, or a FLAP antagonist, or a pharmaceutically acceptable salt thereof, and (c) one or more of a conventional pharmaceutical vehicle, extender, and excipient, and to its use for manufacturing a composition for the treatment of allergic rhinitis, vasomotor rhinitis, and allergic conjunctivitis.

17 Claims, No Drawings

ANTIHISTAMINE LEUKOTRIENE COMBINATIONS

FIELD OF THE INVENTION

The present invention relates to pharmaceutical compositions which contain a nonsedating antihistamine and a substance influencing leukotriene action to improve the local therapy of allergic and/or vasomotor rhinitis and of allergic conjunctivitis.

BACKGROUND

The number of allergic disorders is greatly increasing worldwide. Studies have shown that on average worldwide 7.5% of all children and adolescents suffer from rhinoconjunctivitis which is hay fever combined with an ocular symptomatology (Worldwide variation in prevalence of symptoms of asthma, allergic rhinoconjunctivitis and atopic eczema: ISAAC, Lancet, 351, 1225–1332, 1998). In West European countries, the prevalence, at about 14%, is markedly higher (Annesi-Maesano, I. and Oryszczyn, M. P.: Rhinitis in adolescents, Results of the ISAAC survey, Revue Francaise d'Allergologie et d'Immunologie Clinique, 38, 283–289, 1998; Norrman, E., L. Nystrom, E. Jonsson and N. Stjernberg: Prevalence and incidence of asthma and rhinoconjunctivitis in Swedish teenagers, European Journal of Allergy and Clinical Immunology, 53, 28–35, 1998).

Intensive research activities of recent years have led to the recognition that allergic rhinoconjunctivitis is an inflammatory process in the sense of a persistent inflammatory reaction. While histamine is still regarded as the most important mediator of the early phase and as the most important trigger of the symptoms such as reddening, sneezing, itching and hypersecretion (rhinorrhea and lacrimation), further mediators such as the leukotrienes are involved in the nasal obstruction, secretion and in the progression of the inflammation (e.g. attraction of the proinflammatory cells, promotion of cellular infiltration, etc.). Accordingly, the aims of the therapy have been shifted from symptomatic therapy to an additional antiinflammatory therapy with influencing of the inflammation underlying the allergic disorders. Both histamine and leukotrienes (LTs) are released in the allergic early phase and late phase.

The acute symptoms (itching, reddening, swelling, rhinorrhea and lacrimation) of rhinoconjunctivitis can be readily controlled, inter alia, with the aid of classical antihistamines of the first and second generations. However, they hardly have a therapeutically relevant influence on the inflammation which underlies the disorder and is always progressive. Often, the allergic rhinitis (rhinoconjunctivitis) is regarded both by patients and by the physician as a trivial disorder and accordingly is only inadequately treated. As a result, however, a so-called change of stage can occur, i.e. bronchial asthma, which is to be taken very seriously, develops from the relatively harmless rhinitis. For this reason, it is indispensable to treat even allergic rhinoconjunctivitis adequately and intensively. Only then can the patients live symptom-free and only then can a change of stage, which under certain circumstances is life-threatening, be prevented.

Numerous animal experimental and clinical studies indicate that both histamine and LTs can be detected in nasal secretion (Yamasaki, U., T. Matsumoto, S. Fukuda, T. Natayama, H. Nagaya, Y. Ashida. Involvement of thromboxane $A_2$ and histamine in experimental allergic rhinitis of guinea pigs. J. Pharmacol. Exp. Ther. 82:1046, 1997; Pipkorn, U, G Karlsson, L Enerbeck. Cellular response of the human allergic nasal mucosa to natural allergen exposure. J. Allergy Clin. Immunol. 35:234, 1988; Volovitz, B., S. L. Osur, M. Berstein, P. L. Ogra. Leukotriene $C_4$ release in upper respiratory mucosa during natural exposure to ragweed-sensitive children. J. Allergy Clin. Immunol. 82:414, 1988). Owing to the blockade of the histamine $H_1$ receptors, certain symptoms such as sneezing, reddening, itching and nasal or ocular hypersecretion (rhinorrhea, lacrimation) are significantly reduced (Simons, F. E. R., K. J. Simons. Second generation $H_1$-receptor antagonists. Ann. Allergy 66:5, 1991). In the acute phase of any allergic reaction—independently of the location—degranulation and the emptying of the intracellular stores of the mast cells or of the basophilic granulocytes are prominent. This is a process which is controlled by the extra- or intracellular calcium.

Histamine, however, does not only act as a mediator which induces allergic symptoms, it also acts on the allergic inflammation by influencing the release of cytokines. In a study on human conjunctival epithelial cells (eye), it was shown that histamine greatly increases the secretion of II-8 and GM-CSF (granulocyte macrophage colony stimulating factor). This release can be prevented by histamine $H_1$ receptor antagonists, i.e. this action is mediated via $H_1$ receptors (Weimer, L. K., D. A. Gamache, J. M. Yanni. Histamine-stimulated cytokine secretion from human conjunctival epithelial cells: inhibition by histamine $H_1$-antagonist emedastine. Int. Arch. Allergy Immunol. 115:288, 1998). In addition, we know that allergic stimulation not only releases the intracellularly stored histamine from the mast cells and basophilic granulocytes, but also brings about the de novo synthesis of other mediators such as leukotrienes.

Leukotrienes are mediators which belong to the group of eicosanoids. They are derivatives of arachidonic acid, a fatty acid which is a constituent of membrane phospholipids. The leukotrienes are formed from arachidonic acid via 5-lipoxygenase (5-LOX). At the present time, only the pathogenetically relevant role of the so-called cysteinyl-leukotrienes, to which $LTC_4$, $LTD_4$ and $LTE_4$ belong, has been confirmed. The action of the leukotrienes can take place due to occupation of their receptors or by inhibition of their synthesis. In addition to the inhibition of 5-lipoxygenase, the inhibition of a 5-lipoxygenase-activating protein (hereinafter also referred to as "FLAP") can also lead to decreased synthesis of leukotrienes.

Among the numerous LT antagonists, a few, such as zafirlukast, montelukast, pranlukast, etc. are employed therapeutically in bronchial asthma.

Zileuton is on the market of the 5-LOX inhibitors. The so-called FLAP inhibitors include, for example, MK-591, Bay 1005, which are still in the clinical testing phase.

Numerous investigations confirm the importance of the leukotrienes in allergic disorders. Thus after allergen provocation a marked increase in the LT concentration in the nasal lavage fluid of patients with allergic rhinitis was detected both in the early phase and in the late phase (Creticos, P. S., S. P. Peters, N. F. Adkinson. Peptide leukotriene release after antigen challenge in patients sensitive to ragweed. N. Eng. J. Med. 310:1626, 1984). Cysteinyl-LTs can induce hypersecretion (rhinorrhea or lacrimation), but the leukotrienes appear to be far more important for nasal obstruction.

The nasal obstruction induced by histamine is present in the early phase of the allergic reaction and lasts only minutes, while the obstruction due to leukotrienes can be observed up to the late phase, which lasts 6–8 hours after the allergic provocation. In contrast to histamine, sneezing and itching do not occur after LT provocation (Okuda, M., T. Watase, A. Mazewa, C. M. Liu. The role of leukotrine $D_4$ in allergic rhinitis. Ann. Allergy 60:537, 1988). After provocation with $LTD_4$, however, there is a long-lasting infiltration of eosinophilic granulocytes, which for the greatest part are responsible for the allergic inflammation (Fujika, M. et al. see above).

These so-called late-phase reactions (e.g. nasal obstruction) can be improved by LT antagonists such as zafirlukast (Donnelly, A. L., M. Glass, M. C. Minkwitz, T. B. Casale. The leukotriene $D_4$-receptor antagonist ICI 204219 relieves symptoms of acute seasonal allergic rhinitis. Am. J. Resp. Crit. Care Med. 151:1734, 1995) (ICI 204219= Zafirlukast). The 5-LOX inhibitors are also able markedly to reduce allergic reactions not only in animal experiments, but also in human therapy (Liu, M. C., L. M. Dube, J. Lancaster, and the zileuton study group. Acute and chronic effects of a 5-lipoxygenase inhibitor in asthma: a 6-month randomized multicenter trial. J. Allergy Clin. Immunol. 98:859, 1996).

Azelastine is presently the only active compound among the antihistamines which is available both systemically as a tablet, and topically as nasal spray and eye drops. Accordingly, patients even with very strongly pronounced allergic symptoms can be successfully treated. Patients can be individually treated with various pharmaceutical formulations of azelastine depending on the nature and degree of severity of the symptoms and thus the inflammation underlying the disorder can be suppressed.

Of the modern antihistamines, azelastine was the first in which the inhibition of the synthesis of the leukotrienes important for the allergic inflammatory reaction was observed in therapeutically relevant doses or concentration (Achterrath-Tuckermann, U., Th. Simmet, W. Luck, I. Szelenyi, B. A. Peskar. Inhibition of cysteinyl-leukotriene production by azelastine and its biological significance. Agents and Actions 24: 217, 1988). This antileukotriene effect of azelastine is also detected in controlled clinical studies in allergics (Shin, M. H., F. M. Baroody, D. Proud, A. Kagey-Sobotka, L. M. Lichtenstein, M. Naclerio. The effect of azelastine on the early allergic response. Clin. Exp. Allergy 22:289, 1992). The clinical efficacy of azelastine that is comparable with budesonide, a glucocorticoid, can then also be explained as due to this action. (Wang, D. Y., J. Smitz, M. De Waele, P. Clement. Effect of topical applications of budesonide and azelastine on nasal symptoms, eosinophil counts and mediator release in atopic patients after nasal allergen challenge during the pollen season. Int. Arch. Allergy Immunol. 114:185, 1997; Gastpar, H., R. Aurich, U. Petzold. Intranasal treatment of perennial rhinitis: Comparison of azelastine nasal spray and budesonide nasal aerosol. Arzn. Forsch.—Drug Res. 43:475, 1993).

The action mechanism by which azelastine inhibits LT synthesis and LT release is unique and is not described in the case of other antihistamines. As is known, many release processes proceed through an increased level of intracellular $Ca^{2+}$, which takes place due to allergic stimulation of the effector cells, since intracellular $Ca^{2+}$ initiates the decisive steps for increased leukotriene synthesis and release. Azelastine inhibits intracellular $Ca^{2+}$ release (Takanaka, K. Effects of azelastine on polymorphonuclear leukocytes: arachidonate cascade inhibition mechanism. Progress Med. 275, 1987; Chand, N., et al. Inhibition of allergic and non-allergic leukotriene formation and histamine secretion by azelastine: Implication for its mechanism of action. Int. Arch. Allergy Appl. Immunol. 90:67, 1989; Senn, N., et al. Action of azelastine on intracellular $Ca^{2+}$ in cultured airway smooth muscle. Eur. J. Pharmacol. 205:29, 1991; Chand, N., R. D. Sofia. A novel in vivo inhibitor of leukotriene biosynthesis: A possible mechanism of action: A mini review. J. Asthm. 32:227, 1995).

The mechanism of action of the LT receptor antagonists is simple in that as receptor antagonists, they occupy the LT receptors. Accordingly, the released leukotrienes can approach their receptors and display their actions which can be mediated by the receptor.

Combinations for intranasal application, which contain an antihistamine having leukotriene-inhibiting properties together with a glucocorticosteroid and, if appropriate, decongestants, antiallergics, mucolytics, nonopioid analgesics, lipoxygenase inhibitors and leukotriene receptor antagonists, are disclosed in EP 0 780 127 A1 and are recommended for the treatment of allergic rhinoconjunctivitis. The cooperation of the antihistamine with the glucocorticosteroid is expected to increase the effectiveness of the treatment.

For the topical treatment of rhinitis, WO 98/48839 also discloses the application of an antiinflammatory agent in the form of corticosteroids, with an efficacy increasing addition of, for example, at least a vasoconstrictor, a leukotriene inhibitor, an antihistamine, an antiallergic, a mucolytic, an anaesthetic, an anticholinergic or a neuraminidase inhibitor.

As disclosed in WO 98/34611, for the topical treatment of allergic asthma, combinations are proposed of descarboethoxyloratadine, a metabolite of the nonsedating antihistamine loratadine, and a leukotriene antagonist, which can be a leukotriene $D_4$ antagonist, a 5-lipoxygenase inhibitor or a FLAP antagonist. The use of descarboethoxyloratadine should avoid a large number of undesired side effects of loratadine and other nonsedating antihistamines.

A. Roquet et al. (Combined antagonism of leukotrienes and Histamine produces predominant inhibition of allergen-induced early and late phase airway obstruction in asthmatics. Am. J. Respir. Crit. Care Med., 1997, 155; 1856–1863) investigated the actions of loratadine, the leukotriene antagonist zafirlukast and the combination of both active compounds in allergen-induced airway disorders of asthmatics on oral administration.

From investigations by Merck & Co., WO 97/28797, it is also known to administer loratadine with five selected leukotriene antagonists, monetlukast, zafirlukast, pranlukast, sodium 1-(((R)-3-(2-(6,7-difluoro-2-quinolinyl)ethenyl)phenyl)-3-(2-(2-hydroxy-2-propyl)phenyl)thio)methyl)cyclopropaneacetate, 1 -(((1(R)-3-(2-(2,3-dichlorothieno[3,2-b]pyridin-5-yl)-(E)-ethenyl)phenyl)-3-(2-(1-hydroxy-1-methylethyl)phenyl)propyl)thio)methyl) cyclopropaneacetic acid orally or parenterally in asthma, allergy and inflammations.

A lack of remedial success in the treatment of allergic rhinitis/conjunctivitis, and on account of numerous side effects of introduced preparations, and the nonspecific therapy in some cases, a great need exists for combinations having high effectiveness and safety.

DESCRIPTION OF THE INVENTION

It is an object of the present invention to provide novel combinations for the treatment of allergic rhinitis/conjunctivitis.

The present invention relates to pharmaceutical substance combinations which can be topically administered but also orally in allergic and/or vasomotor rhinitis or allergic conjunctivitis, and containing a nonsedating antihistamine with the exception of loratadine and loratadine metabolites, suitably azelastine, but, for example, also levocabastine, cetirizine, fexofenadine, mizolastine, astemizole, in combination with a leukotriene $D_4$ antagonist which influences leukotriene action, such as montelukast, zafirlukast or pranlukast or with a 5-lipoxygenase inhibitor, such as zileuton, piriprost or AWD 23-115 (1-[4-(quinolin-2-ylmethoxy)benzyl]-5-methoxy-1H-indazol-3-ol dihydrochloride) or with a FLAP antagonist, such as MK-591, MK-886, Bay 1005 respectively, and, if desired, further pharmaceutically acceptable vehicles and/or extenders or excipients therefor.

The present invention furthermore relates to the provision of a process for the prophylaxis and treatment of allergic and/or vasomotor rhinitis or allergic conjunctivitis in a mammalian body, by administering topically or orally to a patient in need therefor a combination of a nonsedating antihistamine with the exception of loratadine or loratadine metabolites, suitably azelastine, and also for example, levocabastine, cetirizine, fexofenadine, mizolastine, astemizole, with a leukotriene $D_4$ antagonist which influences leukotriene action, such as montelukast, zafirlukast or pranlukast or with a 5-lipoxygenase inhibitor, such as zileuton, piriprost or AWD 23–115 or with a FLAP antagonist, such as MK-591, MK-886, Bay 1005 topically or orally. Administration can be carried out simultaneously, sequentially or separately. Therefore, as used throughout the disclosure and claims the term "nonsedating antihistamine" does not include loratadine and loratadine metabolites.

The present invention also relates to suitable individual dosage forms of a nonsedating antihistamine, suitably azelastine but also for example, levocabastine, cetirizine, fexofenadine, mizolastine, astemizole, in combination with a leukotriene $D_4$ antagonist which influences leukotriene action, such as montelukast, zafirlukast or pranlukast or with a 5-lipoxygenase inhibitor, such as zileuton, piriprost or AWD 23–115 or with a FLAP antagonist, such as MK-591, MK-886, Bay 1005, which are suitable for easy topical or oral administration, for example in the form of sprays or drops or tablets.

The novel combination of a nonsedating antihistamine (with the exception of compounds of the loratadine type), suitably azelastine, but also for example, levocabastine, cetirizine, fexofenadine, mizolastine, astemizole and a leukotriene $D_4$ antagonist which influences leukotriene action, such as montelukast, zafirlukast or pranlukast or a 5-lipoxygenase inhibitor, such as zileuton, piriprost or AWD 23-115 or a FLAP antagonist, such as MK-591, MK-886 or Bay 1005, which can also be present as pharmaceutically acceptable salts, can be given, according to the invention, simultaneously, successively or independently of one another, topically (intranasally or intraocularly), or orally as a fixed combination or in individual substances. If separate formulations are present, then these are tailored to one another and contain the respective active compounds in the dosage unit in the same amounts and corresponding weight ratios in which they can be present in the combination.

As a result of the combination, there is not only a rapid onset of action, but also a high therapeutic efficacy, which is accompanied by a strong antiinflammatory action, since the modes of action of the active compounds mentioned are mutually complementary and also behave pharmacokinetically in a similar manner. The long duration of action makes twice daily administration possible. If the active components are present in the form of a fixed combination, administration is simpler for the patient, because both active compounds are contained in one tablet or one container. The concentration of the antihistamine components according to the present invention can be in the range from 0.001% to 0.5%.

The concentration of the leukotriene antagonists in the combination can be in the range from 0.01% to 5%.

Suitable concentrations are 0.05% to 0.2% for the antihistamine component and 0.5% to 2% for leukotriene antagonists.

The intended dosage takes place once to twice daily. The individual dose of the antihistamine is from 50 to 500 μg, suitably from 200 to 400 μg administered topically.

On topical application, the dose of the leukotriene $D_4$ antagonist is between from 100 to 2000 μg, suitably from 200 to 1000 μg.

5-LOX or FLAP inhibitors are administered in a dose range from 50 to 2000 μg, suitably from 200 to 1000 μg.

The dose of the antihistamine (for example azelastine) is between 0.5 and 16 mg/day, suitably 2 and 8 mg/day.

In the case of the leukotriene $D_4$ antagonists (for example montelukast), the individual dose is from 1 to 50 mg/day, suitably from 5 to 10 mg/day.

The oral dose of 5-LOX inhibitors such as zileuton is between 1 and 6 g/day, suitably 0.6 and 2 g/day.

In the case of FLAP inhibitors, the dose is from 50 to 2000 mg/day, suitably from 100 to 500 mg/day.

The specific individual antihistamine and leukotriene antagonist compounds mentioned above, and processes for their preparation are known.

The preparation of the pharmaceutical combinations of the present invention can take place according to customary methods, suitably by mixing the antihistamine and the leukotriene antagonist individually or together, if desired with vehicles and/or extenders or excipients, and converting the mixture thus obtained into suitable forms of administration.

The active compounds are administered orally or topically in the form of a mixture, which contains customary pharmaceutical extenders, excipients or vehicles for pharmaceutical purposes.

The compositions for oral or topical administration can be formulated as different, pharmaceutically acceptable forms of administration, e.g. nasal sprays, nasal drops, eye drops, tablets, capsules or granules. Apart from the active compounds, the compositions according to the present invention can also contain various typical pharmaceutical additives such as antimicrobial preservatives, osmotics, thickening agents, excipients for pH adjustment or buffer systems.

Antimicrobial preservative substances include, for example, benzalkonium chloride, cetylpyridinium chloride/bromide, chlorobutanol, chlorhexidine acetate, chlorhexidine HCl, chlorhexidine digluconate, chlorocresol, methylparaben, propylparaben, phenoxyethanol, phenylmercury salts, sorbic acid, thiomersal.

A combination of sodium edetate and benzalkonium chloride can be suitably used as a preservative. Sodium edetate is used in concentrations of from 0.05 to 0.1%, and benzalkonium chloride in concentrations of from 0.005 to 0.05% wt., based on the composition.

Suitable excipients for adjusting the tonicity or osmolality, sodium chloride, potassium chloride, mannitol, glucose, sorbitol, glycerol or propylene glycol in concentrations of from about 0.1 to about 10% wt. can be used.

The compositions frequently contain thickeners to increase the viscosity and to prolong and to improve the contact between the pharmaceutical ingredient and body tissue. Suitable thickeners include methylcellulose, hydroxypropylmethylcellulose, hydroxyethylcellulose, sodium carboxymethylcellulose, polyvinyl alcohol, polyvinyl-pyrrolidone, polyacrylates, polyacrylamide, dextran, gellan gum, poloxamer or cellulose acetate phthalate.

Moreover, the compositions according to the present invention comprise pharmaceutically acceptable buffers to adjust pH in a range from about 4 to about 8, suitably from about 5.5 to about 7.5. Buffers of this type include citrate, phosphate, tromethamine, glycine, borate or acetate salts. These buffers can also be derived from substances of the type such as citric acid, primary or secondary sodium phosphate, glycine, boric acid, sodium tetraborate, acetic acid and sodium acetate. Moreover, further excipients such as hydrochloric acid or sodium hydroxide can also be used for pH adjustment.

The present invention is further illustrated by the following examples:

EXAMPLE 1

| Nasal spray or nasal drops comprising azelastine hydrochloride (0.1%) | |
|---|---|
| Azelastine hydrochloride | 0.1000 g |
| Hydroxypropylmethylcellulose | 0.1000 g |
| Sodium edetate | 0.0500 g |
| Benzalkonium chloride | 0.0125 g |
| Sodium hydroxide | q.s. pH 6.0 |
| Sorbitol solution 70% | 6.6666 g |
| Purified water | to 100 ml |

Preparation of the Solution:

Introduce about 45 kg of purified water into a suitable stirrer-equipped container.

Add the azelastine HCl, hydroxypropylmethylcellulose, sodium edetate, benzalkonium chloride and sorbitol solution successively thereto and dissolve with stirring. Make up the resulting solution to a volume of 49.5 liters with purified water. Adjust the pH of the solution to pH 6.0 using 1N sodium hydroxide solution. Make up to the final volume of 50.0 liters using purified water and stir. Filter the solution through a membrane filter having a pore size of 0.2 μm and dispense into bottles.

EXAMPLE 2

| Nasal spray or nasal drop suspension containing montelukast (1%) | |
|---|---|
| Montelukast | 1.0000 g |
| Avicel RC 591 | 1.1000 g |
| Polysorbate 80 | 0.1000 g |
| Sorbitol solution 70% | 6.0000 g |
| Sodium edetate | 0.0500 g |
| Benzalkonium chloride | 0.0200 g |
| Purified water | to 100 ml |

Preparation:

Introduce 45 kg of purified water into a suitable stirrer-equipped container having a homogenizing device and homogenize Avicel RC 591 therein at high speed. Then successively dissolve the substances Polysorbate 80, sorbitol solution, sodium edetate and benzalkonium chloride with stirring. Then homogenize in the active compound montelukast at high speed until a uniform suspension results. Then make up to the final volume of 50 liters with purified water and homogenize further. Then evacuate the suspension in order to remove the resulting air bubbles. The resulting suspension is then dispensed into bottles.

EXAMPLE 3

| Nasal spray or nasal drops comprising azelastine hydrochloride (0.1%, dissolved) and montelukast (1%, suspended) | |
|---|---|
| Montelukast | 1.0000 g |
| Azelastine hydrochloride | 0.1000 g |
| Avicel RC 591 | 1.1000 g |
| Polysorbate 80 | 0.1000 g |
| Sorbitol solution 70% | 6.0000 g |
| Sodium edetate | 0.0500 g |
| Benzalkonium chloride | 0.0200 g |
| Purified water | to 100 ml |

Preparation:

Introduce 45 kg of purified water into a suitable stirrer-equipped container having a homogenizing device and homogenize Avicel RC 591 therein at high speed. Then successively dissolve the azelastine hydrochloride active and the excipients Polysorbate 80, sorbitol solution, sodium edetate and benzalkonium chloride with stirring. Then homogenize in the montelukast active at high speed until a uniform suspension results. Then make up to the final volume of 50 liters with purified water and homogenize further. Then evacuate the suspension in order to remove the resulting air bubbles. The resulting suspension is then dispensed into bottles.

From the spectra of action of some antihistamines and also of LT antagonists or 5-LOX and FLAP inhibitors, it can be derived that a combination of both substances displays a synergistic action on the symptoms of allergic rhinoconjunctivitis.

The following pharmacological investigation describes the action of azelastine and montelukast on their own and in combination on a rhinitis model on brown Norway rats. The brown Norway rats were actively sensitized by double i.p. injection of a suspension of ovalbumin and aluminum hydroxide in physiological saline solution on two successive days. Three weeks after sensitization, a catheter was tied into the trachea of the animals in orthograde manner under sodium thiopental anesthesia to maintain the respiration of the animals and a further catheter was advanced in a retrograde manner through the trachea up to the internal opening of the choanas for the perfusion of the nasal cavities and fixed. The nasal perfusate can thus trickle out through the nasal cavities and be accepted by a fraction collector. The test substances were either suspended in Tylose (montelukast) or dissolved in physiological saline solution (azelastine) and injected intraperitoneally 60 min before allergen provocation. PBS was perfused through the nasal cavity for 30 min using a roller pump (perfusion rate 0.5 ml/min) to rinse mucus away from the nose. In the case of topical application, the test substances are added to the perfusate in molar concentration and the solution is perfused through the nose for 30 min before allergen provocation. The plasma marker Evans Blue (1 ml/animal each of a 1% strength solution in PBS) was then injected into the jugular vein. The perfusion was collected during a 15 min break. The allergen provocation (challenge) was then carried out by perfusion of the nasal cavity with a solution of ovalbumin in PBS (10 mg/ml of ovalbumin in PBS) for 60 min, during which the perfusate was collected in the fraction collector in 15 min fractions. The total amount of the samples/animal was 5. The samples were centrifuged and then applied to microtiter plates and measured at a wavelength of 620 nm using the Digiscan photometer. The blank values were automatically subtracted. The course of action over 60 min was calculated using an AUC program. The substance action of the preparation group was calculated in % against vehicle controls.

An increased mucosal permeability after allergen provocation is to be assessed as a sign of the release of messengers such as histamine and leukotrienes. After antigen contact, this phenomenon occurs even in allergic people and is manifested by increased fluid secretion and nasal blockage.

TABLE 1

Action of azelastine and montelukast alone and in combination (intraperitoneal administration) on the nasal mucosal permeability in actively sensitized and topically provoked brown Norway rats

| Substance | Dose (mg/kg, i.p.) | Inhibitory action in % |
|---|---|---|
| Azelastine | 0.01 | 11 |
| | 0.1 | 39 |
| | 0.3 | 42 |
| | 1 | 47 |
| Montelukast | 0.1 | 7 |
| | 1 | 26 |
| | 3 | 39 |
| | 10 | 44 |
| | 30 | 58 |
| Azelastine | 0.01 | |
| + | + | 40* |
| montelukast | 0.1 | |

*p < 0.05

The administration of azelastine alone in a dose of 0.01 mg/kg i.p. causes a small inhibition of the vascular permeability of 11%. Montelukast is likewise slightly active in a dose of 0.1 mg/kg i.p. with 7% inhibition. The combinatory administration of azelastine in a dose of 0.01 mg/kg i.p. and montelukast in a dose of 0.1 mg/kg i.p. caused a superadditive inhibition of the mucosal plasma extravasation of 40% (p<0.05).

Addition of the FLAP inhibitor Bay X 1005 inhibited the nasal mucosal permeability in a dose of 0.1 mg/kg i.p. by 31%. AWD 23–115, and a 5-LOX inhibitor, in a dose range of 0.03 to 10 mg/kg i.p. caused a dose-dependent inhibition (37–54%) of the vascular permeability.

TABLE 2

Action of azelastine and AWD 23-115 alone and in combination (topical application in the perfusate) on the nasal mucosal permeability in actively sensitized and topically provoked brown Norway rats

| Substance | Dose (mmol/l) | Inhibitory action in % |
|---|---|---|
| Azelastine | 0.003 | 3 |
| | 0.01 | 40 |
| | 0.03 | 60 |
| AWD 23-115 | 0.1 | 12 |
| | 0.3 | 32 |
| | 1 | 49 |
| Azelastine | 0.003 | |
| + | + | 31* |
| AWD 23-115 | 0.1 | |

*p < 0.05

On topical application, the histamine $H_1$ blocker azelastine exhibits a strong inhibition of the mucosal plasma extravasation even in concentrations of 0.003 to 0.03 μmol/l. The 5-LOX inhibitor AWD 23–115 inhibits the vascular permeability at 0.3 and 1 μmol/l in a dose-dependent manner by 32% and 49% respectively.

If azelastine is given at a concentration of 0.003 μmol/l in combination with AWD 23–115 (0.1 μmol/l), the inhibition of the mucosal extravasation is 31% (p<0.05).

We claim:

1. A pharmaceutical composition for the treatment of allergic rhinitis, vasomotor rhinitis, and allergic conjunctivitis, which comprises (a) azelastine or a pharmaceutically acceptable salt thereof, (b) a leukotriene $D_4$ antagonist, or a 5-lipoxygenase inhibitor, or a FLAP antagonist, or a pharmaceutically acceptable salt thereof, and (c) one or more of a conventional pharmaceutical vehicle, extender, and excipient.

2. The pharmaceutical composition of claim 1, wherein said leukotriene $D_4$ antagonist is montelukast, zafirlukast or pranlukast.

3. The pharmaceutical composition of claim 1, wherein said 5-lipoxygenase inhibitor is zileuton, piriprost, or AWD 23–115.

4. The pharmaceutical composition of claim 1, wherein said FLAP antagonist is MK-591, MK-886 or Bay X 1005.

5. The pharmaceutical composition of claims 1, wherein the concentration of said azelastine or salt is from 0.001 wt. % to 0.5 wt. % based on the composition.

6. The pharmaceutical composition of claim 1, wherein the concentration of said leukotriene $D_4$ antagonist or salt is from 0.01 wt. % to 5 wt. % based on the composition.

7. The pharmaceutical composition of claim 1, wherein the concentration of said 5-lipoxygenase inhibitor or salt is from 0.01 wt. % to 5 wt. % based on the composition.

8. The pharrmaceutical composition of claim 1, wherein the concentration of the FLAP antagonist.or salt is from 0.01 wt. % to 5 wt. % based on the composition.

9. The pharmaceutical composition of claim 1, wherein the concentration of said leukotriene $D_4$ antagonist, 5-lipoxygenase inhibitor, or FLAP antagonist, or a pharmaceutically acce ptable salt is from 0.01 wt. % to 5 wt. % based on the composition.

10. The pharmaceutical composition of claim 9 in a dosage form for topical administration.

11. The pharmaceutical composition of claim 9 in a dosage form for oral administration.

12. The pharmaceutical composition of claim 1, wherein the dosage form for topical administration is a spray.

13. The pharmaceutical composition of claim 1, wherein the dosage form for topical administration is a nasal or eye drop.

14. A process for treating allergic rhinitis, vasomotor rhinitis, and allergic conjunctivitis, which comprises administering to a patient in need therefor separately or together (a) azelastine or a pharmaceutically acceptable salt thereof and (b) a leukotriene $D_4$ antagonist, or a 5-lipoxygenase inhibitor, or a FLAP antagonist, or a pharmaceutically acceptable salt thereof.

15. The process of claim 14, wherein said nonsedating antihistamine is azelastine, levocabastine, cetirizine, fexofenadine, mizolastine, or astemizole.

16. The process of claim 14, wherein said leukotriene $D_4$ antagonist is zafirlukast, montelukast, or pranlukast, said 5-lipoxygenase inhibitor is zileuton, piriprost, or AWD 23–115, and said FLAP antagonist is MK-591, MK-886, or Bay X 1005.

17. A process for preparing the pharmaceutical composition of claim 1, which comprises combining said azelastine or salt and said component (b) with said component (c) and converting the resulting combination into a dosage form for administration.

* * * * *